United States Patent [19]

Pasquale

[11] 4,066,757
[45] Jan. 3, 1978

[54] ORAL CONTRACEPTIVE REGIMEN
[75] Inventor: Samuel A. Pasquale, Basking Ridge, N.J.
[73] Assignee: Ortho Pharmaceutical Corporation, Raritan, N.J.
[21] Appl. No.: 344,668
[22] Filed: Mar. 26, 1973
[51] Int. Cl.$^2$ .................... A61K 31/56; A61K 31/57; A61K 31/58
[52] U.S. Cl. ................... 424/243; 424/238; 424/241; 424/242
[58] Field of Search ................ 424/238–243

[56] References Cited

U.S. PATENT DOCUMENTS

| 3,409,721 | 11/1968 | Applezweig | 424/239 |
|---|---|---|---|
| 3,568,828 | 3/1971 | Lerner | 206/42 |
| 3,639,600 | 2/1972 | Hendrix | 424/242 |
| 3,733,407 | 5/1973 | Segre | 424/239 |

FOREIGN PATENT DOCUMENTS 2,146,239   3/1972   Germany.

OTHER PUBLICATIONS

Larsson-Cohn et al., ACTA Endocrinologica 63:705–716, (1970), Effects of Continuous Daily Administration of 0.5mg of Chlormadinone Acetate on the Plasma Levels of Progesterone and on the Urinary Excretion of Luteinizing Hormone and Total Oestrogens.
Larsson-Cohn et al., ACTA Endocrinologica 63:216–224, (1970), Effects of Continuous Daily Administration of 0.5mg of Norethindrone on the Plasma Levels of Progesterone and on the Urinary Excretion of Luteinizing Hormone, Pregnanediol and Total Oestrogens.
Rudel et al., I.E.P.T. Sect. 48, vol. 2, Chap. 34:392–394, 411–415, (1972), Oral Contraceptives Progestogens, Purgamon Press N.Y., N.Y.
Rudel et al., Birth Control Contraception and Abortion: 101–130, (1973), Progestogens, Macmillan Co., N.Y., N.Y.

*Primary Examiner*—Shep K. Rose
*Attorney, Agent, or Firm*—Benjamin F. Lambert

[57] ABSTRACT

An oral contraceptive regimen in which a progestin is administered from the fifth through the twenty-fifth day of the physiological cycle is described. The amount of progestin administered is serially increased during the period of administration; regular menses occurs when administration of the regimen is complete.

6 Claims, No Drawings

ORAL CONTRACEPTIVE REGIMEN

The oral contraceptive methods which are currently accepted fall into three categories, i.e. combination cyclic regimens, sequential cyclic regimens and continuous low dose progestin regimens.

In the combination oral contraceptive regimen, an individual daily dose containing both a progestin and estrogen is prescribed for daily use over a period of 20 or 21 days, followed by a 5 to 7 day period when neither is taken to allow for uterine bleeding of a menstrual type. After the bleeding phase, administration of the combination is continued. It is generally accepted that the administration of the ovarian hormones progesterone and estrogen is primarily responsible for suppressing ovulation through inhibition of gonadotropin secretion by the pituitary, as indicated by the reduced urinary pregnanediol excretion during the period of administration. Progestational change in the endometrium is stimulated to the extent that the stroma development progresses occasionally even to the decidual stage.

In the sequential oral contraceptive regimen, an individual daily dosage of estrogen is administered to the patient during the first part of the cycle, i.e. from about day 5 through day 15. Then, in the last 6 or 7 days of the cycle, a combination of estrogen and a progestin is administered as in the combination type. This therapy thus mimics the normal menstrual pattern which is characterized by a rise in estrogen levels during the first part of the cycle, the proliferative phase, and a rise in progestin levels during the second part of the cycle after ovulation, the secretory phase. In the sequential regimen, it is the estrogen which suppresses ovulation by depressing the follicle-stimulating hormone (F.S.H.) levels which in turn prevents the follicles from maturing. Therefore, the luteinizing hormone (L.H.) output of the pituitary has no opportunity to induce ovulation. This is in contrast to the combination oral contraceptive regimen in which both F.S.H. and L.H. pituitary secretion are suppressed. The progestin is also administered during the last six or seven days of treatment to induce changes in the endometrium closely resembling the progesterone influence in the secretory stage of the normal cycle; thus the irregular withdrawal bleeding which is associated with the use of estrogens alone is avoided. At the end of the administration of medication there is a sluffing-off of the endometrial lining in a fashion which mimics normal menstruation.

The third currently used oral contraceptive regimen consists of individual daily doses of small amounts, about 0.35 milligrams, of a progestin, norethindrone, which is administered continuously. Administration of low doses of progestin appears to suppress ovulation in a significant number of women. However, the precise reason for the high degree of effectiveness of such a regimen as a contraceptive is not known. Many investigators believe that it is due to local effects such as the rendering of the cervical mucus inhospitable to sperm during the critical period of the cycle, i.e. the fifth to twenty-fifth day. Regimens based entirely on the progestational activity of the administered compounds have an advantage in that they lack the estrogen component which has been most often associated by some investigators with undesirable side effects. However, in those women in which ovulation is suppressed, the endometrium apparently does not proliferate sufficiently to provide regular menses. In many women using such a regimen, the cycle becomes irregular and has occurred anywhere from the ninth to sixtieth day.

It is an object of this invention to provide an oral contraceptive regimen which retains the advantages of the currently accepted types and overcomes the disadvantages.

It has now been realized that when small, equal, daily doses of progestin are administered to a woman, the level of circulating progestin increases slowly until, after a number of days, the amount of circulating progestin reaches a steady state at a level somewhat above the daily dose. As a result of the circulating progestin, the endometrium will enter the secretory phase. However, once steady state is reached, small changes in environment, food intake or indigenous hormonal fluctuations will cause small variations in the level of circulating progestin. On a day when the level drops sufficiently, withdrawal bleeding occurs. In other words, the onset of menstruation or withdrawal bleeding is not dependent upon the relative amount of circulating progestin present at the pertinent point in the cycle compared to that present at an earlier point in the cycle.

This problem has been solved by means of the present invention which consists of a contraceptive regimen of the type wherein a progestational agent is administered to the human female at regular intervals over at least the fifth through the twenty-fifth day of the cycle. The regimen differs from previously known regimens in that the dose administered at the end, preferably the last 7 days, of the cycle is substantially greater than, and preferably at least twice the dose administered over the fifth through the twelfth day of the cycle. It is preferred that the dosage of the progestational agent during the second week of the regimen be at least double the dosage administered during the first week of the regimen and that the dosage during the third week of the regimen be at least double the dosage administered during the second week of the regimen, and so on thus providing incremental, serial increases in the dosage of progestin. As a result, the level of circulating progestin is essentially rising at all times. When the administration of the progestin is stopped, preferably on the twenty-fifth day of the cycle, substantial and regular menstruation will occur.

Any progestational agent which will otherwise prevent pregnancy when administered continuously in small daily doses may be utilized in such a regimen. Examples of such progestins which are presently being utilized in various contraceptive regimens are: Norethindrone, Norethynodrel, Norgestrel, Ethynodiol Diacetate, Medroxyprogestrone, Chlormadinome Acetate and Dimethistrone. Other progestational agents which may be employed are steroidal oximes such as 17α-ethynyl-17β-acetoxy-19-norandrost-4-en-3-one oxime, ethynodiol diacetate, megestrol acetate, 16α, 17α-dihydroxyprogesterone acetophenonide, 17-hydroxy-19-nor-17α-pregn-5(10)-en-20-yl-3-one, 19-nor-17α-pregn-4-en-20-yne-3β,17-diol, 17-hydroxy-19-nor-17α-pregn-4-en-20-yl-3-one and its acetate, 17-hydroxy-6α-methylpregn-4-ene-3,20-dione and its acetate, 6α,21-dimethyl-17-hydroxy-pregn-4-en-20-yne-3-one, 6-chloro-17α-hydroxy-pregna-4,6-diene-3,20-dione, 9β10α-pregna-4,16-diene-3,20-dione and any other orally active progestin. The preferred progestins are norethindrone and norethindrone acetate oxime.

It will be appreciated that the actual amount of progestin employed is related to the potency of the particular progestin selected for the regimen. Progestational agents which are effective in conventional contraceptive preparations are generally administered in amounts of less than 1 mg. up to about 25 mg. per day depending upon their potency. According to the present invention, it is preferred to use from about 0.2 mg. of progestin in the beginning of the regimen to about 1.5 mg. of progestin at the end of the regimen. It will be readily apparent, however, that lower and higher doses may be administered depending upon whether a strong or weak progestin is employed in the regimen.

The following examples are illustrative of the invention:

EXAMPLE I

Beginning with the fifth day of menstruation, the female is given 0.40 mg. of norethindrone daily for 7 days. The dose is increased to 0.80 mg. daily for the next 7 days, and then further increased to 1.50 mg. for the final 7 days. During the following 7 days, no active agent is administered. A contraceptive effect is achieved and uterine bleeding of a menstrual type occurs. After the twenty-eighth day, the regimen is repeated.

EXAMPLE II

Beginning with the fifth day of menstruation, 0.2 mg. of norethindrone is administered daily for 7 days, 0..4 mg. is administered daily for the next 7 days, and 0.80 mg. is administered daily for the final 7 days. This regimen has the advantage that the average daly dose of norethindrone is 0.4 mg., only slightly greater than the 0.35 mg. daily dose which would otherwise be utilized as a continuous low dose progestin oral contraceptive.

EXAMPLE III

Beginning with the fifth day of menstruation, the female is administered 0.2 gm. of 17α-ethynyl-17β-acetoxy-19-norandrost-4-en-3-one oxime daily for 7 days. The dosage is increased to 0.4 mg. daly for the next 7 days and is then increased to 0.80 mg. daily for the final 7 days. No drug is administered for the following 7 days. A contraceptive effect is achieved and urterine bleeding of a menstrual type occurs. At the end of the seven day period, the regimen is repeated.

EXAMPLE IV

The same procedure is followed using the following dosages of 17α-ethynyl-17β-acetoxy-19-norandrost-4-en-3-one oxime: 0.4 mg daily for 7 days, 0.8 mg daily for 7 days, and 1.5 mg daily for 7 days.

What is claimed:

1. In a method for the prevention of conception of the type wherein a progestin is administered to the human female serially over at least the fifth through the twenty-fifth day of the cycle, the improvement consisting of:
   administering a substantially higher dose of a progestin during approximately the last 7 days of administration than during approximately the first 7 days of administration and terminating the administration of the progestational agent on or after the twenty-fifth day of the cycle.

2. In a method for the prevention of conception of the type wherein a progestin is administered to the human female serially over at least the fifth through the twenty-fifth day of the cycle, the improvement consisting of:
   serially increasing the dose of progestin substantially over the course of administration to thus produce an increasing gradient in the circulating progestin level and then terminating the administration of the progestational agent on or after the twenty-fifth day of the cycle.

3. The method of claim 1 wherein the dose administered at the end of the cycle is at least twice the dose administered over the fifth through the twelfth day of the cycle.

4. The method of claim 1 wherein the dosage of the progestational agent during the second week of the regimen is at least double the dosage administered during the first week, and the dosage administered during the third week is at least double the dosage administered during the second week of the regimen.

5. The method of claim 1 wherein the progestin is 17α-ethynyl-17β-acetoxy-19-norandrost-4-en-3-one-oxime.

6. The method of claim 1 wherein the progestin is norethindrone.

* * * * *

UNITED STATES PATENT AND TRADEMARK OFFICE
CERTIFICATE OF CORRECTION

PATENT NO. : 4,066,757
DATED : January 3, 1978
INVENTOR(S) : Samuel A. Pasquale

It is certified that error appears in the above-identified patent and that said Letters Patent are hereby corrected as shown below:

At Column 2, Line 30, "days,, of" should be -- days, of --.
At Column 3, Line 28, "0..4" should be -- 0.4 --.
At Column 3, Line 31, "daly" should be -- daily --.
At Column 3, Line 40, "daly" should be -- daily --.

Signed and Sealed this

Tenth Day of October 1978

[SEAL]

Attest:

RUTH C. MASON
*Attesting Officer*

DONALD W. BANNER
*Commissioner of Patents and Trademarks*